US012603623B2

(12) United States Patent
Rolff

(10) Patent No.: US 12,603,623 B2
(45) Date of Patent: Apr. 14, 2026

(54) AMPLIFIER DEVICE FOR AMPLIFYING SMALL CURRENTS

(71) Applicant: INFICON GMBH, Cologne (DE)

(72) Inventor: Norbert Rolff, Horrem (DE)

(73) Assignee: INFICON GMBH, Cologne (DE)

( * ) Notice: Subject to any disclaimer, the term of this patent is extended or adjusted under 35 U.S.C. 154(b) by 1112 days.

(21) Appl. No.: 17/438,872

(22) PCT Filed: Mar. 6, 2020

(86) PCT No.: PCT/EP2020/056031
    § 371 (c)(1),
    (2) Date: Mar. 2, 2022

(87) PCT Pub. No.: WO2020/200644
    PCT Pub. Date: Oct. 8, 2020

(65) Prior Publication Data
    US 2025/0192731 A1     Jun. 12, 2025

(30) Foreign Application Priority Data
    Mar. 29, 2019    (DE) .......................... 102019108192.0

(51) Int. Cl.
    *H03F 3/72*        (2006.01)
    *G01N 33/00*       (2006.01)
    *G01R 1/36*        (2006.01)
    *G01R 15/08*       (2006.01)
        (Continued)

(52) U.S. Cl.
    CPC .............. *H03F 3/72* (2013.01); *G01R 15/08* (2013.01); *H03F 3/45475* (2013.01);
        (Continued)

(58) Field of Classification Search
    CPC .... G01R 15/08; G01R 15/09; G01R 19/0061; G01R 19/0062; G01R 19/0092;
        (Continued)

(56) References Cited

U.S. PATENT DOCUMENTS 4,198,607 A     4/1980   Beinitz et al.
4,259,643 A     3/1981   Monticelli et al.
        (Continued)

FOREIGN PATENT DOCUMENTS

CN     102545793 A     7/2012
EP     0615669 B1     9/1999
        (Continued)

*Primary Examiner* — Judy Nguyen
*Assistant Examiner* — James Split
(74) *Attorney, Agent, or Firm* — Kirton McConkie; Whitney Blair

(57)     ABSTRACT

An amplifier device for receiving currents, comprising a first current path for measuring smaller currents of less than 100 pA, an input amplifier device included in the first current path, having at least one first amplifier, an output, an inverting input, a first feedback path connecting the output to the inverting input, and a feedback element included in the first feedback path, wherein the first amplifier has at least one protective element, a second current path for measuring larger currents with a maximum current of at least 10 times the current to be received in the first current path, characterized in that at least one of the protective elements of the amplifier is part of the second current path.

16 Claims, 3 Drawing Sheets

(51) Int. Cl.
    *G01R 19/00*       (2006.01)
    *H03F 3/45*        (2006.01)

(52) U.S. Cl.
    CPC ............ *G01N 33/0027* (2013.01); *G01R 1/36* (2013.01); *G01R 19/0061* (2013.01); *H03F 2200/261* (2013.01); *H03F 2200/426* (2013.01); *H03F 2200/444* (2013.01); *H03F 2200/462* (2013.01); *H03F 2203/45138* (2013.01); *H03F 2203/45518* (2013.01); *H03F 2203/7227* (2013.01)

(58) Field of Classification Search
    CPC .. H03F 3/45475; H03F 3/72; H03F 2200/261; H03F 2200/462; H03F 2203/45138; H03F 2203/45518; H03F 2203/7227
    See application file for complete search history.

(56)              References Cited

U.S. PATENT DOCUMENTS

| | | | |
|---|---|---|---|
| 4,510,442 A | | 4/1985 | Neher |
| 5,543,706 A | * | 8/1996 | Rolff ................ G01R 19/16595 |
| | | | 324/123 R |
| 6,583,421 B2 | | 6/2003 | Harvey |
| 6,897,665 B2 | | 5/2005 | Hung |
| 7,230,431 B2 | * | 6/2007 | Mirme ................... G01R 22/06 |
| | | | 324/123 C |
| 8,278,909 B2 | * | 10/2012 | Fletcher ................ G01R 15/09 |
| | | | 324/123 C |
| 8,415,942 B2 | * | 4/2013 | Fletcher .............. G01R 15/165 |
| | | | 324/123 C |
| 9,086,400 B2 | | 7/2015 | Minch et al. |
| 9,806,685 B1 | | 10/2017 | Hansen |
| 2009/0000236 A1 | | 1/2009 | Schlumpf |
| 2011/0008569 A1 | | 1/2011 | Madok et al. |
| 2017/0030755 A1 | | 2/2017 | Grewal et al. |
| 2022/0376660 A1 | * | 11/2022 | Kirk ......................... H03F 1/52 |

FOREIGN PATENT DOCUMENTS

| | | |
|---|---|---|
| JP | 63-190974 | 8/1988 |
| JP | 05-126864 A | 5/1993 |
| JP | 2010085384 A | 4/2010 |
| JP | 2017-198661 A | 11/2017 |

* cited by examiner

AMPLIFIER DEVICE FOR AMPLIFYING SMALL CURRENTS

RELATED APPLICATIONS

This application is a National Stage of International Application No. PCT/EP2020/056031, filed Mar. 6, 2020, and entitled AMPLIFIER DEVICE FOR AMPLIFYING SMALL CURRENTS, which claims priority to German Patent Application No. DE 10 2019 108 192.0, filed Mar. 29, 2019, which are each incorporated herein by reference in their entirety.

BACKGROUND

In many measuring devices, e.g. in mass spectrometers or vacuum measuring devices, the measured value is formed on the basis of currents which are generated by positively or negatively charged particles impinging on an electrode. The dynamic range of the occurring ion or electron current strength to be measured is very large. The dynamic range often ranges from a few hundred atto-amps to a few micro-amps, thus spanning several decades.

In particular, small currents are to be measured in vacuum measuring devices, in the lower pressure range and in leak detectors. Mass spectrometers are often used for this purpose. For very small currents below 10 fA, circuit difficulties arise when setting up an amplifier that can also measure larger currents at the same time, when range switching from measuring small currents to measuring larger currents is necessary. Current amplifiers using a resistor must include a high-impedance resistor for very small currents, since the current noise of the resistor decreases with increasing values. However, for currents greater than, for example, 10 pA, the high-impedance resistor cannot be used because the voltage drop across the resistor becomes too large. With capacitors as reference components, similar difficulties arise as with resistors. In amplifiers according to prior art, semi-conductor switches or relays are used to switch resistors or current paths to enable switching from an operating state for measuring small currents to an operating state for measuring larger currents. In all cases, additional components are required for this purpose, which are connected to the sensitive input node at which the smallest currents flow and must be measured.

To measure such particle currents, measuring devices are used which generate a measurable measuring potential from the particle current, i.e. ion current or electron current. For this purpose, the measuring device usually has a current amplifier, typically with an operational amplifier. An electrical measuring resistor, arranged for example in the feedback path of the operational amplifier, is used to generate a measurable electrical potential from the amplified current.

In order to cover the entire dynamic range of the occurring particle currents with the same measuring circuit, both the conventional amplifiers and the amplifier according to the invention provide for switching between a sensitive operation for measuring small currents of less than 100 pA (e.g. 1 pA) and an operation for measuring larger currents of at least 1 pA (e.g. 100 pA). In conventional current amplifiers, the switching is done using a relay, for example, in sector field mass spectrometers. In the case of resistor-based current amplifiers covering a large current range, range switching cannot be dispensed with, since only high-impedance resistors can be considered for small currents, while for larger currents, only low-impedance components can carry the large current. For small currents, the resistance noise limits the range of application.

EP 0 615 669 B1 describes an amplifier in which the current signal is transmitted by means of diodes.

SUMMARY

The invention relates to a device and a method for amplifying small currents.

The object of the invention is to provide an amplifier device for amplifying small currents with which switching to amplify larger currents is improved, and to provide a corresponding method.

The amplifier device according to the invention is defined by independent claim 1.

According to the invention, the amplifier device has a first current path for amplifying small currents. The first current path includes an input amplifier device having at least one first amplifier with at least one protective element, e.g. a protective diode, and with a feedback element in a feedback path connecting the output of the input amplifier device to the inverting input. For measuring larger currents, a second current path at least partially different from the first current path is provided and formed. At least one of the protective elements of the first amplifier is included in the second current path.

Thus, according to the invention, an amplifier device is provided at whose input for measuring larger currents no further components are required than those for operation for measuring smallest currents, namely the current input, the measuring resistor in the form of the feedback element and the input amplifier device with at least the first amplifier. The conventionally used input amplifiers already have protective elements, e.g. protective diodes, in the input range, which are required in the integrated circuit to protect the input circuits. According to the invention, said protective elements are used for range switching. Thus, the most sensitive range for measuring the smallest currents of the circuit is as stable as if there were no other ranges for measuring other current quantities. When the range changes from the sensitive range to the range for measuring larger currents, the input current flows through one or more of the protective elements, making the input range low impedance even for much larger input currents. Since protective elements must be present in the integrated circuit of the first amplifier, not every amplifier module can be used. Both amplifier modules that have protective elements to the supply voltages and amplifier modules that have protective elements between the input lines can be used.

The input amplifier device can have a number of n amplifiers with $n \geq 1$. In the simplest case of $n=1$, the input amplifier device includes only the first amplifier. In the case of $n \geq 2$, the input amplifier device can be formed of at least two amplifiers forming an amplifier combination.

The input amplifier device has an inverting input and an output. The output is connected via a feedback path to the inverting input of the input amplifier device. A feedback element is included in the feedback path.

The amplifiers are operational amplifiers and/or the protective elements are protective diodes.

BRIEF DESCRIPTION OF THE SEVERAL VIEWS OF THE DRAWINGS

In the following, exemplary embodiments of the invention are explained in more detail with reference to the figures, in which.

DESCRIPTION OF EMBODIMENTS

Figure 1:
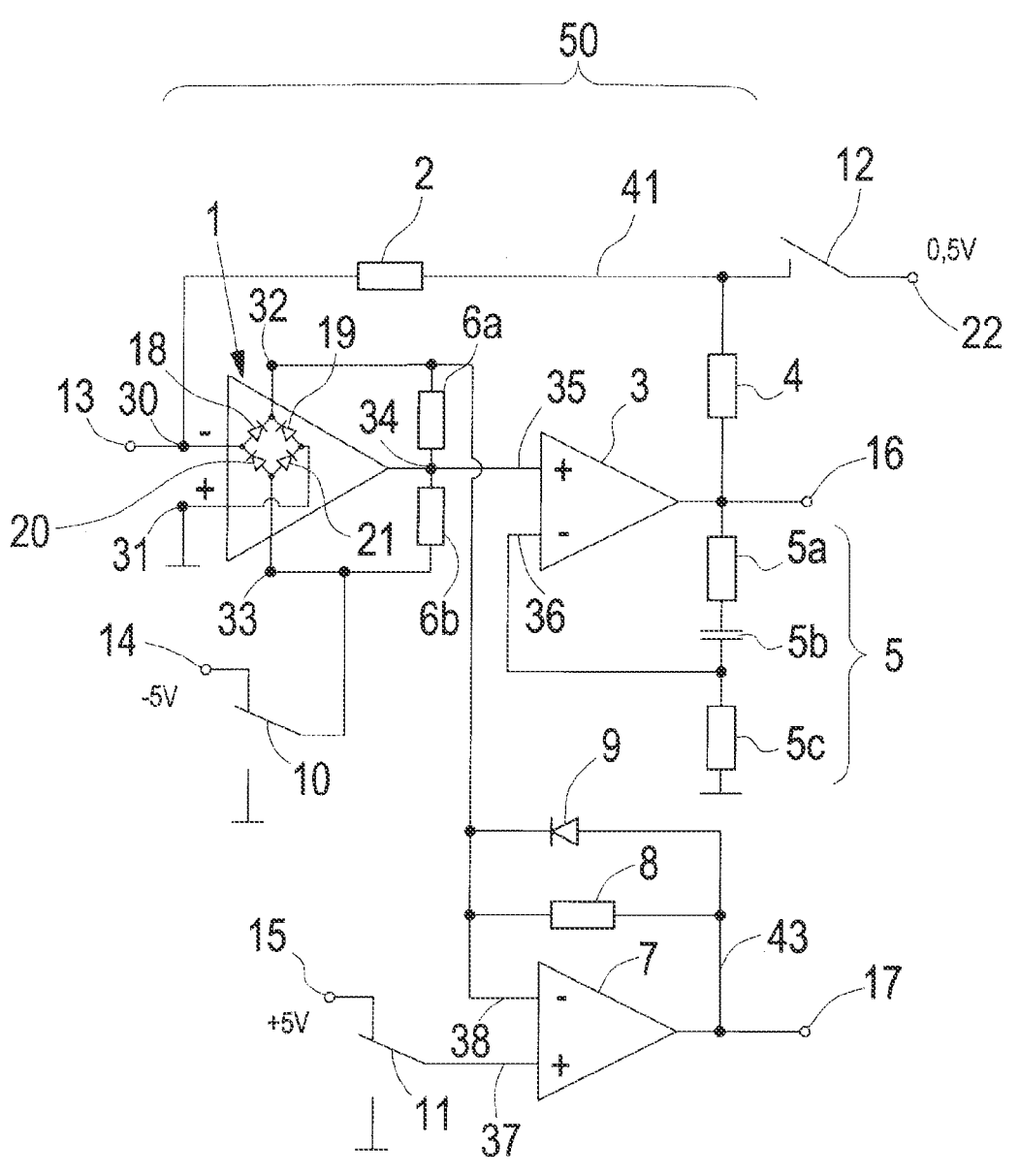
FIG. 1 shows the exemplary embodiment in a first operating state.

The amplifier device of the illustrated exemplary embodiment comprises a first operational amplifier 1 having an inverting input 30, a non-inverting input 31, an output 34, a positive supply connection 32 and a negative supply connection 33.

The operational amplifier includes protective elements 18, 19, 20, 21, in this case diodes, which are arranged in the manner of a bridge rectifier circuit between inverting input 30 and non-inverting input 31 as well as the two supply connections 32, 33 and interconnect them. The diodes 18, 19, 20, 21 are arranged such that they conduct from negative supply connection 33 toward positive supply connection 32 and block in the opposite direction.

The expression "in the manner of a bridge rectifier circuit" means that the bridge branch includes the two inputs 30, 31 of operational amplifier 1. This is based on the idea that in an ideal operational amplifier no voltage is dropped between the two inputs 30, 31. One end of the bridge branch is connected to inverting input 30 and the other end to non-inverting input 31. The differential voltage occurring between the two inputs, which is zero in the ideal operational amplifier, is thus part of the bridge branch.

The output 34 of the first operational amplifier 1 is connected to non-inverting input 35 of a second operational amplifier 3 whose output is connected via a feedback branch 41 to inverting input 30 of the first operational amplifier 1. The feedback path 41 includes two resistors 2, 4 between which feedback path 41 is connected via a third switch 12 to an input 22 to which a voltage of a diode forward voltage of about 0.5 volts is applied.

The output 16 of the second operational amplifier 3 is further connected to ground via control elements 5. The control elements 5 consist of a resistor 5a, a capacitor 5b, and a further resistor 5c. The inverting input 36 of the second operational amplifier 3 is electrically connected for its feedback between capacitor 5b and the further resistor 5c.

The output 34 of the first operational amplifier 1 is connected via a first resistor 6a to positive supply connection 32 of the first operational amplifier 1 and via a second resistor 6b to negative supply connection 33. The negative supply connection 33 is alternately connectable via a first switch 10 to a supply voltage of −5 volts applied to voltage source 14 or ground 10.

The positive supply connection 32 of the first operational amplifier 1 is electrically connected to inverting input 38 of a third operational amplifier 7 whose output 17 is fed back via a resistor 8. The resistor 8 is bridged by a diode 9 which conducts in the direction from output 17 of the third operational amplifier 7 to positive supply connection 32 of the first operational amplifier 1 and blocks in the opposite direction.

The first amplifier 1 and the second amplifier 3 form an input amplifier device 50, wherein both amplifiers 1, 3 form an amplifier combination. The feedback path 41 connects the output of input amplifier combination 50 to its inverting input 30.

The non-inverting input 37 of the third operational amplifier 7 is selectively connectible via a second electric switch 11 to a voltage source 15, in this case 5 volts, or to ground.

In the illustrated exemplary embodiment of the amplifier device according to the invention, the first operation amplifier 1 is used as the input amplifier, the protective elements 18, 19, 20, 21 of which are provided as input protective diodes to the supply voltage. If the amplifier device is operated for measuring small currents, of, for example, less than 100 pA in the most sensitive range, the input current signal reaches the first operational amplifier 1 via input 13. The first operational amplifier 1 receives the negative supply voltage from voltage source 14 via the first switch 10 in the switch position shown in FIG. 1. The operational amplifier 1 receives the positive supply voltage from voltage source 15, in this case amounting to +5 volts, via the second switch 11 in the switch position shown in FIG. 1 at non-inverting input 37 of the third operational amplifier 7.

The output voltage at output 17 of the third operational amplifier 7 regulates itself to a value increased by the diode forward voltage of diode 9. As a result, the voltage reaching the first operational amplifier 1 becomes as large as the voltage at non-inverting input 37 of the third operational amplifier 7.

The amplifier 7 is not part of input amplifier device 50. The amplifier 7 serves for receiving larger current at input 13 of input amplifier device 50. The input current flows through diode 18 through amplifier 1 directly to input 38 of amplifier 7. Smaller currents at input 13, however, are first amplified by input amplifier device 50.

The third electric switch 12 is open in this operating state shown in FIG. 1 for measuring small currents. The feedback resistors 4, 2 together form the feedback element, in this case in the form of an electrical resistor.

In this case, input 13 at inverting input 30 of the first operational amplifier 1 represents a virtual zero point, which means that no significant voltage is present at input 13.

An inverted voltage proportional to the input current of the first operational amplifier 1 is applied to output 16 of the second operational amplifier 3. The protective diodes 18, 19, 20, 21 of the input amplifier are now each operated in the reverse direction and thus do not carry any appreciable current.

The input amplifier device 50 from the first operational amplifier 1 and the second operational amplifier 3 form a control circuit. The control elements 5 must be dimensioned depending of the cut-off frequency of the used elements 5a, 5b, 5c so that the circuit remains stable, e.g. 120 kOhm at electrical resistor 5a, 1 nF at capacitor 5b and 10 kOhm at electrical resistor 5c.

Figure 2:
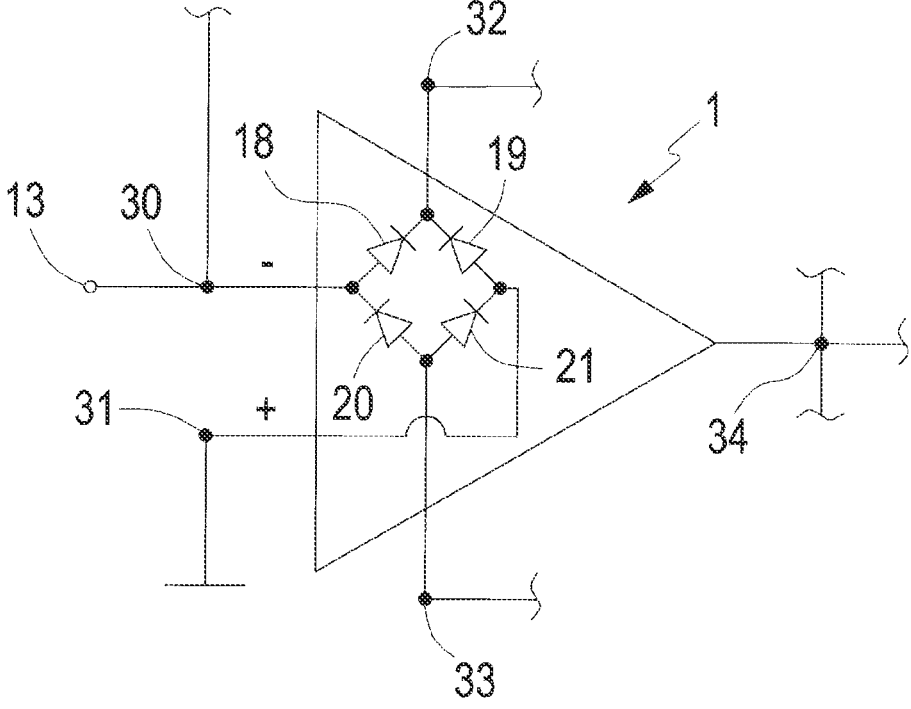
FIG. 2 shows a detail of FIG. 1.

FIG. 1 shows the entire amplifier device, while FIG. 2 shows in detail the first operational amplifier 1 and the protective elements 18, 19, 20, 21 arranged therein and their electrical interconnection with the connections of the first operational amplifier 1.

Figure 3:
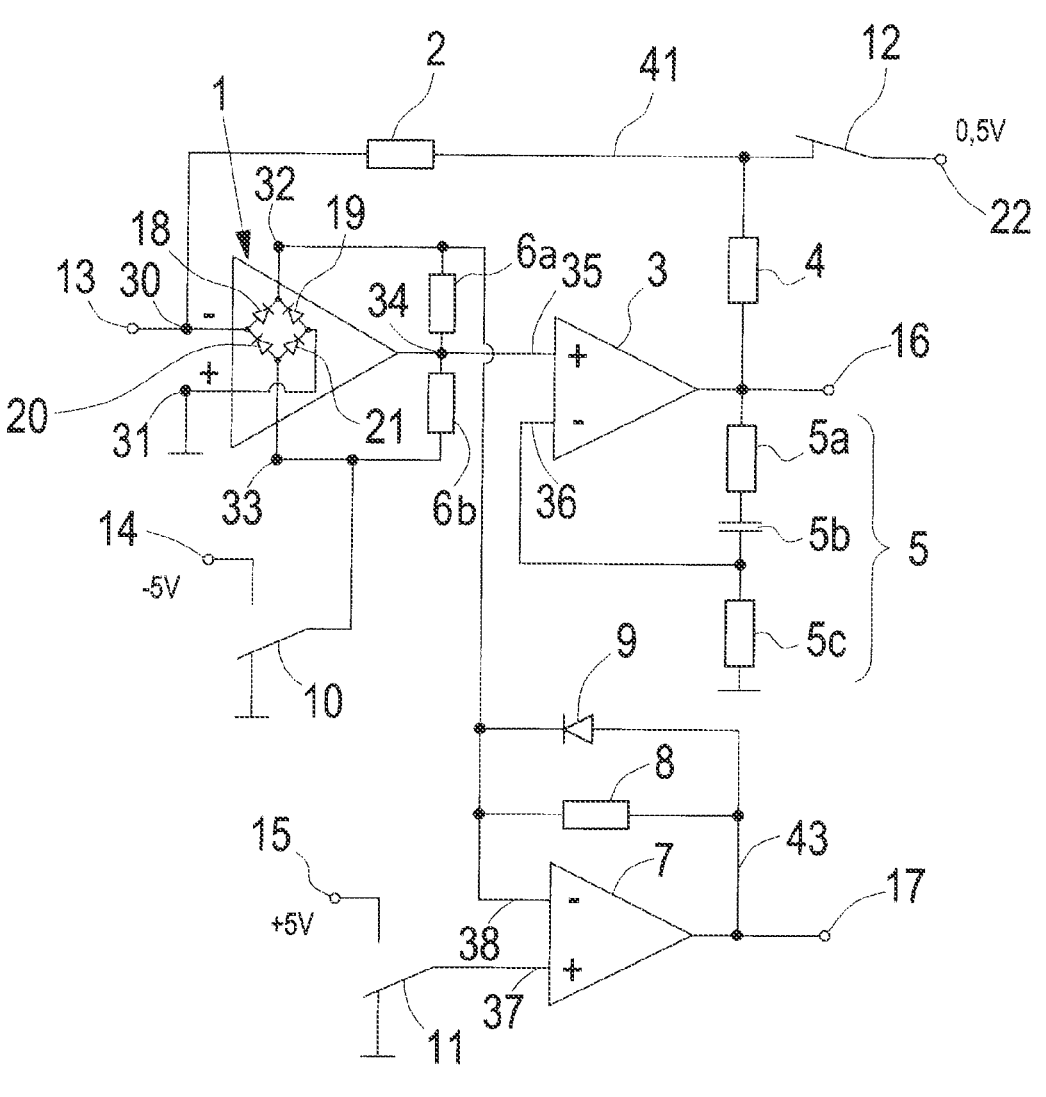
FIG. 3 shows the exemplary embodiment in a second operating state.

FIG. 3 shows the amplifier device in the operating state for measuring larger currents via the second current path. For this purpose, the amplifier device is operated in an extended current range in which the first electric switch 10 is switched to ground potential. Thus, a voltage of approximately 0 volts is applied to negative supply connection 33 of the input amplifier. The input protective elements 20, 21 continue to block.

The second switch 11 is also switched to ground potential. Since the third operational amplifier 7 regulates itself with its feedback resistor 8 such that there is no appreciable differential voltage between inverting input 38 and non-inverting input 37 of the third operational amplifier 7, the positive supply of the first operational amplifier 1 at positive supply connection 32 will also be close to 0 volts. Now, when an input current is applied to input connection 13, it will flow through protective diode 18 to positive supply connection 32.

The third electric switch 12 is closed in this operating condition so that the voltage applied to connection 22, in this case 0.5 volts, is applied to feedback resistor 2 in accordance with the diode forward voltage of protective diode 18 so that as little current as possible flows through feedback resistor 2.

The second current path for larger currents at input 13 now leads via protective diode 18 to feedback resistor 8 of the third operational amplifier 7. An inverted voltage proportional to the input current is applied across feedback resistor 8, which can be tapped at output 17 of the third operational amplifier 7. In this case, diode 9 blocks. The second current path for measuring larger currents then leads from inverting input 30 of the first operational amplifier 1 via a protective diode 18 of the protective diodes 18, 19, 20, 21 to positive supply connection 32 of the first operational amplifier 1 and from there via feedback resistor 8 of the third operational amplifier 7 to its output connection 17.

In the described circuit arrangement, input voltage 13 is increased by the forward voltage of protective element 18 when operating in the current path for larger currents. To avoid this characteristic, the ground points on switches 10 and 11 can be lowered by the forward voltage of protective element 18. In this case, feedback element 2 is currentless when 220 volts are applied to the input.

Figure 4:
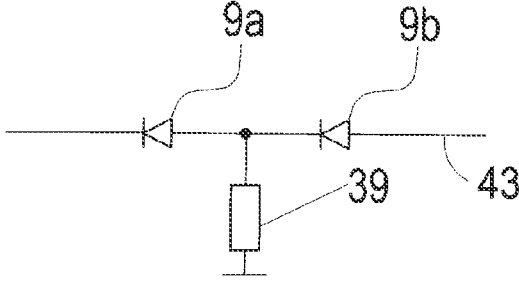
FIG. 4 shows a detail of FIG. 1 or FIG. 3 according to a second exemplary embodiment.

A further improvement of the second current path results when diode 9 is divided according to FIG. 4. In the case where the second current path has been activated, a negative voltage is applied to output 17. The reverse current of the diode falsifies the measurement. If the circuit is complemented according to FIG. 4, the negative voltage at diode 9b drops. Approximately zero volts are then applied to both sides of diode 9a, which significantly reduces the reverse current.

The circuit for positive input currents has been described here. In principle, a circuit variant for negative or also both current directions is possible.

The invention claimed is:

1. An amplifier device for receiving currents, comprising a first current path adapted to measure small input currents of less than 100 pA when said input current flows through said first current path, an input amplifier device included in the first current path, comprising at least one first amplifier, an output, an inverting input, a first feedback path connecting the output to the inverting input, and a feedback element included in the first feedback path, wherein the first amplifier comprises at least one protective element in the first current path, a second current path adapted to measure larger input currents when said input current flows through said second current path with a maximum input current of at least 10 times the input current to be received in the first current path, said second current path being at least partially different from said first current path, wherein, at least one of the protective elements of the input amplifier device in the first current path is also part of the second current path such that when a measuring range changes from a range for measuring small input currents in the first current path to a range for measuring large input currents in the second current path, the input current flows through the at least one protective element comprised in the first and second current paths.

2. The amplifier device according to claim 1, wherein a supply voltage of the first amplifier is applied to at least one of the protective elements.

3. The amplifier device according to claim 1, wherein at least one of the protective elements is arranged between two inputs of the first amplifier and connected thereto.

4. The amplifier device according to claim 1, wherein the feedback element in the first feedback path is an electrical resistor.

5. The amplifier device according to claim 1, wherein the feedback element in the first feedback path is a capacitor.

6. The amplifier device according to claim 1, wherein the input amplifier device comprises at least one further amplifier forming a control loop with the first amplifier.

7. The amplifier device according to claim 1, wherein at least one of two supply connections of the first amplifier is connected via an electrical resistor to the output of the first amplifier.

8. The amplifier device according to claim 1, wherein a feedback path connects the output of a last amplifier of the input amplifier device consisting of the first amplifier and at least one further amplifier to the inverting input of the input amplifier device.

9. The amplifier device according to claim 1, wherein a negative supply connection of the first amplifier is selectively connectible via a first switch to a negative supply voltage or ground, while a positive supply connection of the first amplifier is electrically conductively connected to an inverting connection of a third amplifier, a non-inverting input of which is selectively connectible via a second switch to a positive supply voltage or ground.

10. The amplifier device according to claim 9, wherein a third amplifier comprises a second feedback path with an electrical resistor and an electrical diode arranged in parallel with the resistor and conducting in the direction from the output of said third amplifier to the positive supply connection of the first amplifier and blocking in the opposite direction.

11. The amplifier device according to claim 9, wherein the first feedback path is selectively connectible via a third switch to a voltage which avoids or allows current flow in the feedback element depending on the switch position.

12. The amplifier device according to claim 9, wherein ground references of the first switch and the second switch and a reference voltage are changed by a forward voltage of the protective element.

13. The amplifier device according to claim 10, wherein a second feedback path comprises two diodes between which a resistor leads with respect to the second switch.

14. A gas detector comprising a mass spectrometric sensor or a total pressure sensor and an amplifier device according to claim 1.

15. A method for measuring currents by using an amplifier device according to claim 1, wherein switching from the first current path to the second current path takes place by connecting a negative supply connection of the first amplifier to ground.

16. The method according to claim 15, wherein, for switching the current path, a non-inverting input of a third amplifier, whose inverting input is connected to a positive supply connection of the first amplifier, is additionally connected to ground.

* * * * *